(12) United States Patent
Marhold et al.

(10) Patent No.: US 6,333,434 B1
(45) Date of Patent: Dec. 25, 2001

(54) PREPARATION OF TRIFLUOROMETHYLANILINES

(75) Inventors: Albrecht Marhold, Leverkusen; Käthe Baumann, Köln, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/707,180

(22) Filed: Nov. 6, 2000

(30) Foreign Application Priority Data

Nov. 10, 1999 (DE) .................................. 19954014

(51) Int. Cl.[7] .............................................. C07C 209/00
(52) U.S. Cl. ................................................. 564/417
(58) Field of Search ............................................ 564/417

(56) References Cited

U.S. PATENT DOCUMENTS

| | | |
|---|---|---|
| 2,086,029 | 7/1937 | Heyna . |
| 4,469,890 | * 9/1984 | Chupp et al. ................. 564/417 |
| 5,471,002 | 11/1995 | Appel et al. . |
| 5,831,128 | 11/1998 | Beller et al. . |

OTHER PUBLICATIONS

J. Chem. Soc., May 26, 1961, pp. 1477–1480, Morris Freifelder et al, "Effect of Nuclear Substitution on the Reaction of Aromatic Amines with Ethylene Oxide".
J. Org. Chem., Apr. 27, 1962, pp. 1406–1409, Maynard S. Raasch, "The Chemistry of Sulfur Tetrafluoride. IX. Reaction with Amino Acids in Hydrogen Fluoride[1]".
J. Chem. Soc., Perkin Trans 1 (month unavailable), 1988, pp. 921–926, Gillian E. Carr, et al,
"Sodium Perfluoroalkane Carboxylates as Sources of Perfluoroalkyl Groups".
J. Am. Chem. Soc., 69, (month unavailable), 1947, pp. 2346–2350, Reuben G. Jones, "Ortho and Para Substituted Derivatives of Benzotrifluoride".
J. Org. Chem. 44, (month unavailable, 1979, pp. 4731–4733, Linda P. Seiwell, "Copper–Catalyzed Nonaqueous Ammonolysis of ρ–Chlorobenzotrifluoride. Effect of Potassium Fluoride [1]".
Synthesis, Nov. 11, 1992, pp. 1087–1089, George A. Olah et al, "Aromatic Nitration with Nitric Acid/Trifluoromethanesulfonic Anhydride[1]".

* cited by examiner

*Primary Examiner*—Alan Siegel
(74) *Attorney, Agent, or Firm*—Joseph C. Gil; Richard E. L. Henderson

(57) ABSTRACT

The invention relates to a process for the preparation of trifluoromethylanilines of formula (I)

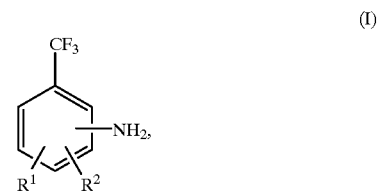

(I)

wherein
$R^1$ is hydrogen, fluorine, chlorine, bromine, methyl, monochloromethyl, dichloromethyl, or formyl, and
$R^2$ is hydrogen, fluorine or chlorine,
with the proviso that when $R^1$ and $R^2$ are both hydrogen, the amino group is para to the trifluoromethyl group, comprising
(a) nitrating a benzotrichloride of formula (II)

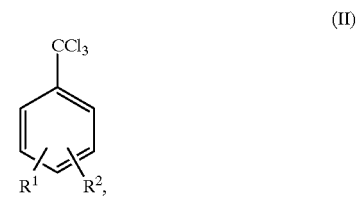

(II)

wherein $R^1$ and $R^2$ are each as defined for formula (I), thereby forming a nitrobenzotrichloride,
(b) converting the trichloromethyl group of the nitrobenzotrichloride into a trifluoromethyl group by reaction with anhydrous hydrofluoric acid, thereby forming a nitrobenzotrifluoride, and
(c) reducing the nitro groups of the nitrobenzotrifluoride to form a trifluoromethylaniline of formula (I).

11 Claims, No Drawings

PREPARATION OF TRIFLUOROMETHYLANILINES

The present invention relates to an improved process for preparing trifluoromethylanilines starting from benzotrichlorides.

Trifluoromethylanilines are important intermediates for preparing pharmaceutically and agrochemically active compounds, for example herbicides, insecticides, infection inhibitors and disinfectants. There is therefore a need for a process for preparing trifluoromethylanilines in a simple and economical manner in industrial quantities in good yields and purities.

Existing processes for preparing trifluoromethylanilines are unsuitable for practice on an industrial scale or have other serious disadvantages.

The use of sulphur tetrafluoride for preparing trifluoromethylanilines on an industrial scale (see J. Org. Chem. 26, 1477 (1961) and 27, 1406 (1962)) is not advisable on account of its extreme toxicity.

The introduction of trifluoromethyl groups by means of sodium trifluoroacetate in the presence of stoichiometric amounts of copper(I) iodide (see J. Chem. Soc. Perk. Trans. 1, 1988, 921) requires costly reagents, and there are problems with the disposal of copper salts.

The fluorination of tribromomethylnitrobenzene with antimony trifluoride and the subsequent reduction of the resulting trifluoromethylnitrobenzene by means of tin chloride (see J. Am. Chem. Soc. 69, 2346 (1947)) likewise requires costly reagents and substantial spending on ecological measures.

The reaction of chlorobenzotrifluoride with ammonia and copper(I) chloride (see J. Org. Chem. 44, 4731 (1979)) requires drastic reaction conditions and provides only low yields.

Nitrating benzotrifluoride and reducing the nitrobenzotrifluoride obtainable provides large amounts of 3-trifluoromethylaniline (around 90%), some 2-trifluoromethylaniline (around 9%) and only little 4-trifluoromethylaniline (around 1%) (see Synthesis 11, 1087 (1992)). The situation is similar with the nitration of substituted benzotrifluorides. The only processes in existence for preparing 3-chloro-6-nitrobenzotrifluoride and 3-fluoro-6-nitrobenzotrifluoride (US-A 2,086,029) provide 3-chloro-4-nitrobenzotrifluoride and 3-fluoro-4-nitrobenzotrifluoride only "to a small extent". Frequently, however, the 4-trifluoromethylanilines are the more wanted compounds.

Preparing trifluoromethylaniline by catalytic reduction of trifluoromethylnitrobenzene has been known for a long time (see J. Org. Chem. 26, 1477 (1964)), but, as explained above, 4-trifluoromethylnitrobenzene is not conveniently obtainable on an industrial scale.

A more recent process for preparing trifluoromethylaniline comprises reacting trichloromethylphenyl isocyanate first with anhydrous hydrofluoric acid and then with water to obtain trifluoromethylaniline hydrofluoride, from which the free aniline is released using a base (see EP-A 639 556). The starting isocyanate has to be prepared first, for example by chlorination of methylphenyl isocyanate. The particular disadvantage of this process is its many stages.

Another recent process reacts chlorobenzotrifluoride with ammonia or amine in the presence of a palladium catalyst, a cocatalyst and a strong base (see EP-A 846 676). As well as being complex, the process has the disadvantage that even an isomerically pure starting material will give rise to a product that is a mixture of isomers.

This invention now provides a process for preparing trifluoromethylanilines of the formula (I)

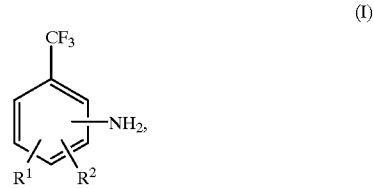

(I)

where
R$^1$ is hydrogen, fluorine, chlorine, bromine, methyl, monochloromethyl, dichloromethyl or formyl and
R$^2$ is hydrogen, fluorine or chlorine and for R$^1$=R$^2$= hydrogen the amino group is para to the trifluoromethyl group, characterized in that a benzotrichloride of the formula (II)

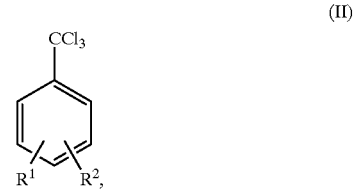

(II)

where
R$^1$ and R$^2$ are each as defined for the formula (I),
is nitrated and, in the nitrobenzotrichlorides thus obtainable, the trichloromethyl groups are converted into trifluoromethyl groups by reaction with anhydrous hydrofluoric acid and finally the nitro groups are reduced.

In the formulae (I) and (II) R$^1$ is preferably hydrogen, fluorine or chlorine and R$^2$ is preferably hydrogen or chlorine.

The first step of the process according to the invention, the nitration of benzotrichlorides of the formula (II), is preferably carried out using mixtures of nitric acid and sulphuric acid as nitrating agent, the sulphuric acid preferably being at least 96% strength and the nitric acid being fuming nitric acid containing around 100% HNO$_3$. The nitric acid is preferably used in excess, for example 1.2 to 5 mol per mole of benzotrichloride of the formula (II). This amount is preferably 1.8 to 2.5 mol. The weight ratio of nitric acid to sulphuric acid can be for example 0.5 to 2:1. It is also possible first to add just nitric acid and then sulphuric acid. An addition of sulphuric acid without initially charging or simultaneously adding nitric acid to benzotrichlorides of the formula (II) is to be avoided.

The nitration can be carried out for example at temperatures in the range −15 to +50° C. It is preferable to use the range from −10 to +35° C. If desired, the nitration may be carried out in the presence of an inert solvent. Examples of useful solvents are dichloromethane and 1,2-dichloroethane.

The nitration can be carried out batchwise of discontinuously or else continuously, for example in a tubular reactor. The use of bundle reactors or microreactors is likewise possible.

The as-nitrated reaction mixture can be worked up, for example, by discharging it onto ice, extracting with an inert organic solvent, washing the combined extracts acid-free (for example with water and/or aqueous sodium bicarbonate solution), drying and removing the extractant.

The second step of the process according to the invention, the reaction with anhydrous hydrofluoric acid, can be carried out using the mixture of isomeric nitrobenzotrichlorides obtained in the first step. However, it is also possible first to separate the isomers, for example by distillation or crystallization, and to react isomerically pure nitrobenzotrichlorides with anhydrous hydrofluoric acid.

For example, 3 to 50 mol of anhydrous hydrofluoric acid can be used per mole of nitrobenzotrichloride, in which case the material commercially available under the name "anhydrous hydrofluoric acid" is sufficiently water-free.

The fluorination can be carried out for example at temperatures in the range 0 to 180° C. and pressures in the range 1 to 50 bar. It is preferable to fluorinate at 10 to 160° C. and 1 to 30 bar. If desired, the fluorination can be carried out in the presence of a catalyst and/or an inert solvent. The catalyst used can be for example boron trifluoride, titanium tetrachloride, antimony pentachloride or antimony pentafluoride, while dichloromethane can be used as solvent.

The anhydrous hydrofluoric acid can be charged first and the nitrobenzotrichloride added, or vice versa. It is advantageous to combine the hydrofluoric acid and the nitrobenzotrichloride at relatively low temperatures, for example, at up to 50° C., within the framework of the abovementioned temperature ranges, and then to increase the temperature. After the reaction has ended, the reaction mixture can be admixed with a suitable solvent, for example dichloromethane, and the organic phase separated off, washed with water, dried and concentrated or distilled.

The fluorination can also be carried out in the gas phase, in which case the reaction temperature can be 200 to 450° C. for example.

To prepare very isomerically pure trifluoromethylanilines of the formula (I), it is advantageous to separate the isomers at the nitrobenzotrifluoride stage. For example, this separation of isomers may be effected by final distillation or a combination of final distillation and crystallization. The final distillation is preferably carried out using such pressures that the liquid phase does not have to be heated to temperatures above 200° C. It is advantageous to carry out the final distillation at pressures in the range 50 to 150 mbar and at liquid phase temperatures in the range from 110 to 180° C. A combination of final distillation and crystallization can be carried out for example by first isolating an at least 80% pure product by final distillation and using it to obtain even purer products by crystallization. The crystallization mother liquor can be recycled into the final distillation. This makes it possible for example to obtain 4-nitrobenzotrifluoride in a purity above 99% and to use it to prepare in the third stage a similarly pure 4-trifluoromethylaniline. The crystallization may be carried out for example simply by cooling or by addition of a solvent in which the trifluoromethylanilines are sparingly soluble. If desired, the product obtained by crystallization can be further purified by recrystallization.

The third step of the process according to the invention, the reduction, can be carried out in a conventional manner, for example as a chemical reduction using for example hydrazine hydrate, ammonium formate, triethylamine/formic acid, tin(II) chloride, iron, sodium sulphide or sodium hydrogensulphide as reducing agent.

However, preference is given to the catalytic reduction with hydrogen in the presence of catalysts, for example Raney nickel or palladium catalysts. The catalytic reduction can be carried out for example at temperatures in the range from 20 to 100° C., pressures in the range from 1 to 50 bar and optionally in the presence of solvents such as alcohols or esters, preferably $C_1$–$C_4$-alkyl alcohols or acetates thereof The catalytic hydrogenation is generally accompanied by significant isomerization, i.e. in general isomerically pure or substantially isomerically pure trifluoromethylanilines are obtained when a corresponding isomerically pure or substantially isomerically pure nitrobenzotrifluoride has been used. Nitrobenzotrifluorides in the form of isomeric mixtures generally give rise to trifluoromethylaniline isomer mixtures having the same or similar distribution of isomers.

To obtain isomerically pure trifluoromethylanilines, it is advantageous to carry out the separation of isomers prior to the reduction stage.

The mixture present after a catalytic reduction can be worked up in a simple manner, for example by filtering it and subsequently concentrating the filtrate. A chemical reduction can be worked up in the manner which is known in principle for such reactions.

The process of the invention is a simple way of preparing trifluoromethylanilines in good yields and purities in few reaction steps and in customary apparatus. It also provides trifluoromethylanilines containing higher levels of 4-isomers than in the prior art. Problematic reagents such as sulphur tetrafluoride and costly reagents such as bromides or iodides need not be used. There are no special ecological problems.

This is surprising, since using benzotrifluorides (instead of benzotrichlorides) as starting materials provides worse results, as is reflected for example in the high fraction of 3-isomers (around 90%). Specifically the separation of the 3- from the 4-isomers is particularly inconvenient because of the small boiling point differences. The significantly smaller quantities of 3-isomers produced in the process of the invention can likewise be obtained in very pure form (after removal of the other isomers at the nitro compound stage) and used as intermediates for active pharmaceuticals and agrochemicals. It is also possible to separate off unwanted isomers at the nitrobenzotrichloride stage and to convert them into the corresponding nitrobenzoyl chlorides which are not accessible from the benzotrifluorides. The invention also provides access to compounds previously obtainable only with difficulty, if at all, such as 3,4-dichloro-5-trifluoromethylaniline, 3,4-dichloro-2-trifluoromethylaniline and the corresponding nitro compounds.

The invention converts benzotrichlorides of the formula (II) into products that include at least 19% of 4-trifluoromethylanilines (formula (I), $N_2$ para to $CF_3$).

EXAMPLES

Example 1

A mixture of 96% by weight sulphuric acid (564 g) and 100% fuming nitric acid (564 g) was admixed with benzotrichloride (1000 g) at −7 to 0° C. by dropwise addition over 4 hours. The reaction mixture was then initially warmed to 10° C. for 30 minutes, then discharged onto ice and finally extracted with dichloromethane (3×500 ml). The combined organic phases were washed with water (500 ml), saturated aqueous sodium bicarbonate solution (3×500 ml) and aqueous sodium chloride solution (500 ml), dried over magnesium sulphate and evaporated, leaving a liquid product (1207 g, purity 98.5%, 96.7% of theory) which was 80.6% 3-nitrobenzotrichloride and 19.4% 4-nitrobenzotrichloride.

Example 2

A mixture of 96% by weight sulphuric acid (2.26 kg) and 100% filming nitric acid (2.26 kg) was admixed with benzotrichloride (4000 g) at 0° C. by dropwise addition over 4 hours. The reaction mixture was then initially warmed to 10° C. for 30 minutes, then discharged onto ice and finally extracted with dichloromethane (3×200 ml). The combined organic phases were washed with water (2000 ml), saturated aqueous sodium bicarbonate solution (3×2000 ml) and aqueous sodium chloride solution (2000 ml), dried over magnesium sulphate and evaporated, leaving a liquid product (4.4 kg, purity 94.6%, 84.6% of theory) which was 75% 3-nitrobenzotrichloride and 25% 4-nitrobenzotrichloride.

Example 3

A mixture of 96% by weight sulphuric acid (48 g) and 100% fuming nitric acid (48 g) was admixed with 3-chlorobenzotrichloride (100 g) at 10 to 20° C. by dropwise addition over 15 minutes. The reaction mixture was then initially stirred at 20 to 30° C. for 2 hours, then discharged onto ice and finally extracted with dichloromethane (3×100 ml). The combined organic phases were washed with water 100 ml), saturated aqueous sodium bicarbonate solution (3×100 ml) and aqueous sodium chloride solution (100 ml), dried over magnesium sulphate and evaporated, leaving a product (115.63 g, purity 100%, 96.7% of theory) which was 26.3% 3-chloro-4-nitrobenzotrichloride and 73.7% 3-chloro-6-nitrobenzotrichloride.

Example 4

A mixture of 52 g of 95% by weight sulphuric acid and 52 g of 100% fuming nitric acid was admixed with 100 g of 3-fluorobenzotrichloride at 10 to 20° C. by dropwise addition over 15 minutes. The reaction mixture was then initially stirred at 30 to 40° C. for 2 hours, then discharged onto ice and finally extracted 3× with 100 ml of dichloromethane. The combined organic phases were washed with 100 ml of water, 3×100 ml of saturated aqueous sodium bicarbonate solution and 100 ml of aqueous sodium chloride solution, dried over magnesium sulphate and evaporated, leaving 110 g of crude product (purity 100%, 90.7% of theory) which was 3.2% 3-fluoro-4-nitro-, 0.3% 3-fluoro-5-nitro- and 96.5% 3-fluoro-6-nitro-benzotrichloride. It was recrystallized from cyclohexane to obtain 100% pure 3-fluoro-6-nitro-benzotrichloride, mp. 57 to 59° C. (98 g, 81.2% of theory), the other isomers ending up in the residue.

Example 5

A mixture of 62 g each of 96% by weight sulphuric acid and 100% fuming nitric acid was admixed with 100 g of 2,3-dichlorobenzotrichloride at 10 to 20° C. by portionwise addition over 15 minutes. The reaction mixture was then initially stirred at 30 to 40° C. for 1 hour, then discharged onto ice and extracted with 3×100 ml of dichloromethane. The combined organic phases were washed with 100 ml of water, 3×100 ml of saturated aqueous sodium bicarbonate solution and 100 ml of aqueous sodium chloride solution, dried over magnesium sulphate and evaporated, leaving a crude product (109 g, purity 100%, 93.4% of theory) which was 92.7% 2,3-dichloro-5-nitro- and 7.3% 2,3-dichloro-6-nitro-benzotrichloride.

Example 6

A mixture of 62 g each of 96% by weight sulphuric acid and 100% by weight fuming nitric acid was admixed at −5° C. with a solution of 100 g of 2,3-dichlorobenzotrichloride in 120 ml of dichloromethane added dropwise over 20 minutes. The reaction mixture was initially stirred at 20 to 30° C. for 2 hours and then refluxed for 2 hours. Subsequently the mixture, which had become solid in the meantime, was placed on ice and extracted with 3×100 ml of dichloromethane. The combined organic phases were washed with 100 ml of water, 3×100 ml of saturated aqueous sodium bicarbonate solution and 100 ml of aqueous sodium chloride solution, dried over magnesium sulphate and evaporated. The crude product (99 g, purity 100%, 84.4% of theory) was recrystallized from ethanol to selectively obtain 80 g (=68.1% of theory) of 2,3-dichloro-5-nitrobenzotrichloride (mp. 97 to 99° C.), the other isomers ending up in the residue.

Example 7

62 g of fuming nitric acid were added dropwise to 100 g of 2,3-dichlorobenzotrichloride at −10 to +10° C. in the course of 10 minutes, followed by 62 g of 96% by weight sulphuric acid. The reaction mixture was initially stirred at 20 to 30° C. for 2 hours, then cooled down, discharged onto ice and extracted 3× with 100 ml of dichloromethane each time. The combined organic phases were washed with 100 ml of water, 3×100 ml of saturated aqueous sodium bicarbonate solution and 100 ml of aqueous sodium chloride solution, dried over magnesium sulphate and evaporated. The crude product (99 g, purity 100%, 84.4% of theory) was recrystallized from ethanol to obtain 68 g (=58.2% of theory) of 2,3-dichloro-5-nitro-benzotrichloride (mp. 97 to 99° C.), while the other isomers ended up in the residue.

Example 8

1138 g of the 3- and 4-nitro-benzotrichloride mixture obtained according to Example 1 were added dropwise to 850 ml of anhydrous hydrofluoric acid at an internal temperature of between 2 and 7° C. in the course of 15 minutes. This was followed by stirring for 17 hours at room temperature and for 8 hours at 150° C. and 25 bar pressure, cooling down to room temperature and distillative removal of excess hydrofluoric acid. The residue was distilled to obtain 695 g of a mixture of 3- and 4-nitrobenzotrifluoride (purity 100%, 76.8% of theory). This mixture was separated by final distillation to obtain 521.6 g of 3-nitrobenzotrifluoride and 110.5 g of 4-nitrobenzotrifluoride each in a purity of above 99%.

The nitrobenzotrichloride mixtures obtained according to Examples 2 to 4 were fluorinated and separated by distillation in a similar manner and with similar yields.

Example 9

406 g of a 3- and 4-nitrobenzotrifluoride mixture obtained according to Example 8 (prior to the final distillation) and 44 g of Raney nickel were initially charged in 4 l of methanol and subjected to a hydrogen pressure of 5 bar at 20° C. for 65 hours and then of 10 bar at 20° C. for 40 hours. Thereafter, the reaction mixture was filtered and the filtrate evaporated to obtain a product (330 g, purity 87.6%, 84.5% of theory) which was 78% 3- and 22% 4-aminobenzotrifluoride.

Example 10

110 g of a 4-nitrobenzotrifluoride (purity above 99%) obtained according to Example 8 (after the final distillation) and 10 g of Raney nickel were initially charged in 1 l of methanol and subjected to a hydrogen pressure of 10 bar at 20° C. for 40 hours. Thereafter, the reaction mixture was filtered and the filtrate evaporated to obtain 80.0 g (=86.3% of theory) of 4-trifluoromethylaniline in a purity of above 99%.

What is claimed is:

1. A process for preparing trifluoromethylanilines of formula (I)

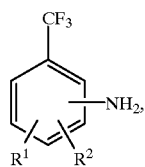
(I)

wherein
$R^1$ is hydrogen, fluorine, chlorine, bromine, methyl, monochloromethyl, dichloromethyl, or formyl, and
$R^2$ is hydrogen, fluorine or chlorine,
with the proviso that when $R^1$ and $R^2$ are both hydrogen, the amino group is para to the trifluoromethyl group, comprising
(a) nitrating a benzotrichloride of formula (II)

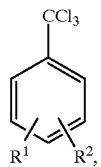
(II)

wherein $R^1$ and $R^2$ are each as defined for formula (I), thereby forming a nitrobenzotrichloride,
(b) converting the trichloromethyl group of the nitrobenzotrichloride into a trifluoromethyl group by reaction with anhydrous hydrofluoric acid, thereby forming a nitrobenzotrifluoride, and
(c) reducing the nitro groups of the nitrobenzotrifluoride to form a trifluoromethylaniline of formula (I).

2. The process of claim 1 wherein in formulas (I) and (II) $R^1$ is hydrogen, fluorine, or chlorine and $R^2$ is hydrogen or chlorine.

3. The process of claim 1 wherein the benzotrichloride is nitrated using mixtures of nitric acid and sulphuric acid in which the sulphuric acid is at least 96% strength and the nitric acid contains around 100% $HNO_3$.

4. The process of claim 3 wherein from 1.2 to 5 mol of nitric acid are used per mole of benzotrichloride of formula (II).

5. The process of claim 3 wherein the weight ratio of nitric acid to sulphuric acid is 0.5 to 2:1 and the nitration is carried out in the range −15 to +50° C.

6. The process of claim 1 wherein 3 to 50 mol of anhydrous hydrofluoric acid are used per mole of nitrobenzotrichloride and the fluorination is carried out at temperatures in the range 0 to 180° C. and pressures in the range 1 to 5 bar.

7. The process of claim 1 wherein an isomer separation is carried out after formation of the nitrobenzotrifluoride in step (b).

8. The process of claim 1 wherein the reduction of the nitro group is carried out by a catalytic reduction with hydrogen in the presence of a Raney nickel catalyst.

9. The process of claim 1 wherein the reduction of the nitro group is carried out by a catalytic reduction with hydrogen in the presence of a palladium catalyst.

10. The process of claim 1 wherein the reduction of the nitro group is carried out at temperatures in the range from 20 to 100° C.

11. The process of claim 1 wherein the reduction of the nitro group is carried out at pressures in the range 1 to 50 bar.

* * * * *